United States Patent [19]

Haglid

[11] 4,159,391

[45] Jun. 26, 1979

[54] PROCESS FOR PREPARING 1,4-DICHLORO-2,5-DIMETHOXYBENZENE

[75] Inventor: Frank R. Haglid, Wilmington, Del.

[73] Assignee: E. I. Du Pont de Nemours and Company, Wilmington, Del.

[21] Appl. No.: 872,091

[22] Filed: Jan. 25, 1978

[51] Int. Cl.² ............................................. C07C 41/00
[52] U.S. Cl. .................................................. 568/649
[58] Field of Search ..................................... 260/613 D

[56] References Cited

U.S. PATENT DOCUMENTS 3,363,005  1/1968  Alvarez ................................. 260/613

Primary Examiner—Bernard Helfin

[57] ABSTRACT p-Dimethoxybenzene is dissolved in monochlorobenzene and reacted with elemental chlorine in the presence of concentrated sulfuric acid catalyst to give 1,4-dichloro-2,5-dimethoxybenzene.

3 Claims, No Drawings

PROCESS FOR PREPARING 1,4-DICHLORO-2,5-DIMETHOXYBENZENE

This invention relates to the chlorination of p-dimethoxybenzene. More particularly, it relates to an improved process for chlorinating p-dimethoxybenzene by dissolving this compound in monochlorobenzene and reacting elemental chlorine with the p-dimethoxybenzene at about 0° to 100° C. in the presence of concentrated sulfuric acid catalyst.

U.S. Pat. No. 3,363,005 discloses and claims an improved process for preparing 1,4-dichloro-2,5-dimethoxybenzene, an agricultural fungicide, in which carbon tetrachloride is used as solvent and aluminum chloride treated with methanol is the catalyst in the chlorination reaction. Because extraordinary methods are required to control environmental and health risks associated with the use of carbon tetrachloride, a process which uses an alternate reaction system is economically desirable. Further, if higher yields can be achieved, such a system is even more attractive.

SUMMARY OF THE INVENTION

The present invention provides an improved process for chlorinating p-dimethoxybenzene to form 1,4-dichloro-2,5-dimethoxybenzene in which the improvement comprises dissolving the p-dimethoxybenzene in monochlorobenzene and reacting elemental chlorine with the p-dimethoxybenzene at 0° to 100° C. in the presence of concentrated sulfuric acid catalyst, the sulfuric acid being present in a concentration of 1 to 15 parts per 100 parts of p-dimethoxybenzene.

The process of this invention increases the yield of 1,4-dichloro-2,5-dimethoxybenzene and improves process operability.

DETAILED DESCRIPTION OF THE INVENTION

In the process of this invention, p-dimethoxybenzene is dissolved in monochlorobenzene with agitation. Sulfuric acid is added, as catalyst, followed by introduction of liquid or gaseous chlorine.

The concentration of p-dimethoxybenzene can vary from about 0.1 to about 45 percent by weight. Lower concentrations are impractical because of the unusually large reactor required to operate the process commercially. Higher concentrations cause difficulties in subsequent process steps such as with an aqueous wash because a three-phase system can form. In a preferred embodiment of this invention, the concentration of p-dimethoxybenzene is about 20 to 34 percent by weight.

The catalyst is 95 to 98 percent concentrated sulfuric acid which can be present in the reaction in a concentration of about 1 to 15 parts per 100 parts of p-dimethoxybenzene. In a preferred embodiment of this invention the concentration of sulfuric acid will range from about 2 to 6 parts per 100 parts of p-dimethoxybenzene. Lower sulfuric acid concentrations can result in the formation of undesirable phenolic by-products (as determined by non-aqueous titration of weakly acidic impurities in the product.) At higher concentrations of sulfuric acid, sulfonation of the monochlorobenzene and p-dimethoxybenzene increases which reduces the yield.

Liquid or gaseous chlorine is introduced into the system below the surface of the reaction mixture along with rapid agitation. Two to 2.1 moles of elemental chlorine per mole of p-dimethoxybenzene is used, preferably 2.05 moles of elemental chlorine. The reaction is carried out at atmospheric pressure and at a temperature in the range of about 0° to 100° C. In a preferred embodiment of this invention the temperature is about 20° to 50° C. The reaction time depends on the efficiency of heat removal from the reaction mass and can vary from a few minutes to several hours.

The process of this invention, which is more particularly described in the following example, allows more flexibility in process operation. As described in the prior art, the correct chlorine charge is critical since overchlorination results in formation of the trichloro-derivative of the product. In the improved process of this invention, overchlorination attacks primarily the two minor dichloro-isomers, and there is therefore a greater margin for error in determining the chlorination and end point.

EXAMPLE 1

Exactly 100 parts by weight of p-dimethoxybenzene were dissolved in 387 parts by weight of monochlorobenzene in a glass vessel equipped with an agitator, a water jacket for heating or cooling, a hydrogen chloride off-gas scrubber and a gas inlet tube for the introduction of chlorine gas. A quantity of 4.2 parts by weight of concentrated sulfuric acid was then added. While maintaining a reaction temperature of 30°–40° C. by jacket cooling, 105 parts by weight of chlorine gas were added over a period of 90 minutes. The charge was then heated to 70° C. by applying steam to the reactor jacket, and this temperature was maintained while the batch was washed successively with water, 5 percent by weight sodium hydroxide and again water. Distillation of monochlorobenzene is then started at atmospheric pressure. When about 70 percent of the monochlorobenzene had been removed from the reaction mass, and the vessel temperature is about 152° C., slow steam sparging was started. The vessel temperature was held between about 140°–150° C. When about 20 parts by weight of steam had been introduced, the reaction mass was nearly free of monochlorobenzene. The molten reaction product was then poured into a tray and allowed to solidify. Product composition is shown in Table 1.

Table 1

| Composition | Concentration % by weight |
| --- | --- |
| monochlorodimethoxybenzene | 0.4 |
| 1,3-dichloro-2,5-dimethoxybenzene | 1.7 |
| 1,4-dichloro-2,5-dimethoxybenzene | 93.3 |
| 1,2-dichloro-3,6-dimethoxybenzene | 2.2 |
| trichlorodimethoxybenzene | 1.9 |
| tetrachlorodimethoxybenzene | 0 |
| non-volatiles | 0.3 |
| phenolics | 0.4 |
| yield (based on dimethoxybenzene) | 92.3 |

The embodiments of the invention in which an exclusive property or privilege is claimed are defined as follows:

1. In a process for chlorinating p-dimethoxybenzene to form 1,4-dichloro-2,5-dimethoxybenzene, the improvement comprising dissolving the p-dimethoxybenzene in monochlorobenzene and reacting elemental chlorine with the p-dimethoxybenzene at a temperature of about 0°–100° C. using 2.0 to 2.1 moles of chlorine per mole of p-dimethoxybenzene in the presence of concentrated sulfuric acid catalyst, the sulfuric acid being present in a concentration of 1–15 parts per 100 parts of p-dimethoxybenzene.

2. The process of claim 1 in which the elemental chlorine is reacted with p-dimethoxybenzene at 20°–50° C. and the sulfuric acid is present in a concentration of 2 to 6 parts per 100 parts of p-dimethoxybenzene.

3. The process of claim 2 in which the elemental chlorine is reacted with p-dimethoxybenzene using 2.0 to 2.08 moles of elemental chlorine per mole of p-dimethoxybenzene.

* * * * *